US010667869B2

(12) United States Patent
Kotian et al.

(10) Patent No.: US 10,667,869 B2
(45) Date of Patent: Jun. 2, 2020

(54) GUIDANCE SYSTEM FOR NEEDLE PROCEDURES

(71) Applicant: General Electric Company, Schenectady, NY (US)

(72) Inventors: Francois Kotian, Buc (FR); Thomas McCarthy, Paris (FR)

(73) Assignee: General Electric Company, Schenectady, NY (US)

( * ) Notice: Subject to any disclaimer, the term of this patent is extended or adjusted under 35 U.S.C. 154(b) by 347 days.

(21) Appl. No.: 15/597,370

(22) Filed: May 17, 2017

(65) Prior Publication Data

US 2018/0333208 A1 Nov. 22, 2018

(51) Int. Cl.
| | | |
|---|---|---|
| *A61B 34/20* | (2016.01) | |
| *A61B 6/00* | (2006.01) | |
| *A61B 6/12* | (2006.01) | |
| *A61B 6/03* | (2006.01) | |
| *A61B 34/10* | (2016.01) | |
| *A61B 90/00* | (2016.01) | |

(Continued)

(52) U.S. Cl.
CPC .............. *A61B 34/20* (2016.02); *A61B 6/032* (2013.01); *A61B 6/12* (2013.01); *A61B 6/4441* (2013.01); *A61B 6/466* (2013.01); *A61B 6/487* (2013.01); *A61B 6/5205* (2013.01); *A61B 6/587* (2013.01); *A61B 6/589* (2013.01); *A61B 90/13* (2016.02); *A61B 90/36* (2016.02); *A61B 6/4085* (2013.01); *A61B 2034/107* (2016.02); *A61B 2034/2055* (2016.02); *A61B 2090/365* (2016.02); *A61B 2090/367* (2016.02); *A61B 2090/376* (2016.02); *A61B 2090/3966* (2016.02); *A61B 2090/502* (2016.02)

(58) Field of Classification Search
CPC . A61B 6/4085; A61B 90/13; A61B 2090/061; A61B 2034/2055
See application file for complete search history.

(56) References Cited

U.S. PATENT DOCUMENTS

| | | | |
|---|---|---|---|
| 5,553,112 A * | 9/1996 | Hardy | A61B 6/08 378/206 |
| 5,598,269 A | 1/1997 | Kitaevich et al. | |

(Continued)

FOREIGN PATENT DOCUMENTS

| | | |
|---|---|---|
| GB | 2324736 B | 2/2001 |
| GB | 2384439 B | 6/2004 |

(Continued)

OTHER PUBLICATIONS

Hamamatsu Handbook "X-ray detectors" ch. 9, (2015) p. 14. (Year: 2015).*

(Continued)

*Primary Examiner* — Bill Thomson
*Assistant Examiner* — Aminah Asghar (57) ABSTRACT

Systems and methods for surgical tool navigation, include a movable gantry. A light emitting device is connected to the movable gantry. A range meter connected to the gantry. The distance meter measures a distance between the light emitting device and a surface. In a method of surgical tool navigation, the light emitting device projects light on the surface. The range meter detects the light and measures the distance between the light emitting device and the surface.

15 Claims, 9 Drawing Sheets

(51) Int. Cl.
*A61B 90/13* (2016.01)
*A61B 90/50* (2016.01)

(56) References Cited

U.S. PATENT DOCUMENTS

| | | | |
|---|---|---|---|
| 5,957,934 | A | 9/1999 | Rapoport |
| 6,041,249 | A | 3/2000 | Regn |
| 6,096,049 | A | 8/2000 | McNeirney et al. |
| 6,487,431 | B1 | 11/2002 | Iwano et al. |
| 8,165,660 | B2 | 4/2012 | Pfister et al. |
| 8,265,731 | B2 | 9/2012 | Kukuk et al. |
| 8,600,138 | B2 | 12/2013 | Gorges et al. |
| 9,076,255 | B2 | 7/2015 | Benson et al. |
| 9,351,758 | B2 | 5/2016 | Baldwin et al. |
| 9,370,627 | B2 | 6/2016 | Kukuk et al. |
| 2003/0099328 | A1 | 5/2003 | Jensen et al. |
| 2003/0208122 | A1* | 11/2003 | Melkent ............ A61B 5/06 600/426 |
| 2005/0004580 | A1* | 1/2005 | Jokiniemi ............ A61B 90/17 606/130 |
| 2005/0124988 | A1* | 6/2005 | Terrill-Grisoni ............ A61B 17/3403 606/53 |
| 2006/0222143 | A1 | 10/2006 | Du et al. |
| 2006/0269114 | A1 | 11/2006 | Metz |
| 2007/0021668 | A1 | 1/2007 | Boese et al. |
| 2007/0270690 | A1* | 11/2007 | Woerlein ............ A61B 90/36 600/429 |
| 2008/0171936 | A1 | 7/2008 | Homan et al. |
| 2008/0200876 | A1 | 8/2008 | Kukuk et al. |
| 2008/0208041 | A1* | 8/2008 | Gilboa ............ A61B 6/12 600/426 |
| 2009/0171244 | A1 | 7/2009 | Ning et al. |
| 2009/0274271 | A1* | 11/2009 | Pfister ............ A61B 6/12 378/62 |
| 2010/0014740 | A1 | 1/2010 | Movassaghi et al. |
| 2011/0082467 | A1* | 4/2011 | Tien ............ A61B 90/06 606/130 |
| 2011/0282188 | A1* | 11/2011 | Burnside ............ A61B 8/0841 600/424 |
| 2012/0085893 | A1* | 4/2012 | Miyamoto ............ B23Q 17/2461 250/221 |
| 2012/0140875 | A1 | 6/2012 | Dennerlein et al. |
| 2012/0250964 | A1 | 10/2012 | Pfister |
| 2012/0289825 | A1 | 11/2012 | Rai et al. |
| 2012/0300910 | A1 | 11/2012 | Gorges et al. |
| 2014/0107473 | A1 | 4/2014 | Dumoulin et al. |
| 2014/0161222 | A1* | 6/2014 | Tsuyuki ............ G01N 23/046 378/19 |
| 2014/0357986 | A1* | 12/2014 | Baldwin ............ A61B 5/065 600/424 |
| 2015/0208948 | A1* | 7/2015 | Wei ............ A61B 5/066 600/424 |
| 2016/0015470 | A1* | 1/2016 | Border ............ G02B 27/017 600/117 |
| 2016/0275684 | A1 | 9/2016 | Elenbaas et al. |
| 2017/0055928 | A1 | 3/2017 | Taron et al. |
| 2019/0117187 | A1* | 4/2019 | Patel ............ A61B 17/3403 |

FOREIGN PATENT DOCUMENTS

| | | |
|---|---|---|
| WO | 2014185746 A1 | 11/2014 |
| WO | 2015121301 A1 | 8/2015 |

OTHER PUBLICATIONS

Borst et al., "Accuracy of X-Ray Image-Based 3D Localization from Two C-Arm Views: A Comparison Between an Ideal System and a Real Device", Feb. 6, 2009.

Holm et al., "In vivo assessment of bifurcation optimal viewing angles and bifurcation angles by three-dimensional (3D) quantitative coronary angiography", The International Journal of Cardiovascular Imaging, Dec. 2011.

Kitslaar et al., "Automated determination of optimal angiographic viewing angles for coronary artery bifurcations from CTA data—art. No. 69181J", Proceedings of Spie—The International Society for Optical Engineering, Mar. 2008.

Papalazarou et al., "Surgical Needle Reconstruction Using Small-Angle Multi-View X-Ray", International Conference on Image Processing, Sep. 2010.

* cited by examiner

GUIDANCE SYSTEM FOR NEEDLE PROCEDURES

BACKGROUND

The present discloser relates to the field of needle procedure guidance systems. More specifically, the present disclosure relates to an optical based system for needle procedure guidance.

Needle based interventional procedures, for example biopsies, cementoplasties, thermal ablations, or transpendicular screw placement, are guided by imaging systems. Imaging guidance systems may include those based upon ultrasound, computed tomography (CT) or interventional X-ray.

In interventional X-ray guided needle procedures, preoperative 3D imaging, for example CT, and/or intraoperative 3D imaging, for example cone beam computed tomography (CBCT), are used to plan the intervention. Planning the intervention entails locating the target of the intervention and planning a needle target trajectory to the located target. Plain fluoroscopy and fluoroscopy fused with planning imaging are used intraprocedure to guide the needle insertion and progress to the target. This is for example available in the Innova Track Vision product available from GE Healthcare. The needle can also be reconstructed from two radioscopic projections to enhance the CBCT image and show progress of the needle to the target. This is for example provided by the Stereo 3D product available from GE Healthcare.

Needle insertion may also be guided by laser light which materializes the optical axis of the X-ray imaging system and guides the needle insertion into the patient in a "bullseye" view. External laser alignment devices may be used to guide needle insertion along a trajectory which does not coincide with the X-ray imaging system optical axis. However, these systems require alignment with the patient bed and are further loosely integrated with the X-ray imaging system.

BRIEF DISCLOSURE

Systems and methods of laser guided needle procedures improve upon current technologies and methods which use fluoroscopic imaging to locate the needle tip in relation to the target intraprocedure. While fluoroscopic imaging may be used in conjunction with laser guided needle procedures, the use and resulting radiation dose can be reduced and/or eliminated in a manner that can also avoid the use of complex magnetic or optical needle navigation systems.

An exemplary embodiment of a system for surgical tool navigation includes a moveable gantry. A light emitting device is connected to the moveable gantry. A distance meter is connected to the movable gantry. The distance meter measures a distance between the light emitting device and a surface, which may exemplarily be the skin of a patient or a puncture point of a surgical tool.

In another exemplary embodiment, the system for surgical tool navigation further includes a system controller. The system controller is operatively connected to the movable gantry. The system controller operates the movable gantry to align a beam of light emitted from the light emitting device with a target trajectory for a surgical tool.

In another exemplary embodiment of the surgical tool navigation system, the system controller receives a measurement of a distance between a surgical tool and the light emitting device by the distance meter. The system controller calculates an estimate of a position of a tip of the surgical tool from the measurement.

In a still further exemplary embodiment the system for surgical tool navigation, an X-ray source is secured to the movable gantry. The X-ray source is configured to emit X-rays. An X-ray detector is secured to the movable gantry. The X-ray detector is configured to receive emitted X-rays. A system controller is operatively connected to the moveable gantry, the X-ray source, the X-ray detector, and the distance meter. The system controller operates to receive measured distances between the light emitting device and a skin surface of a patient as the gantry rotates about the patient to acquire medical image of the patient. The system controller calculates an estimate of a skin surface of the patient from the measured distances.

An exemplary embodiment of a method of surgical tool navigation includes providing a movable gantry. The moveable gantry includes a light emitting device and a distance meter. The light emitting device is operated to project a beam of light at a surface. A distance between the surface and the light emitting device is measured with the distance meter.

In another exemplary embodiment of the method of surgical tool navigation, the beam of light is aligned with a target trajectory for a surgical tool by changing the angle of the X-ray emitter to the receptor axis.

In a further exemplary embodiment of a method of surgical tool navigation, the method additionally includes an X-ray source and an X-ray detector connected to the moveable gantry. The X-ray detector is connected to the light emitting device. The X-ray source and X-ray detector are operated to acquire a plurality of medical images as the movable gantry rotates the X-ray source and the X-ray detector. Distances between the light emitting device and a skin surface of a patient are measured as the moveable gantry rotates the X-ray source and the X-ray detector. A cross-sectional circumference of the patient is modeled from the measured distances.

In an additional exemplary embodiment, a length of the surgical tool is measured by measuring with the distance meter a first distance between light projected from the light emitting device on a reference surface and the light emitting device and a second distance between the light projected from the light emitting device on a surgical tool handle and the light emitting device.

In another exemplary embodiment, a length of the surgical tool is received. A location of a tip of the surgical tool is estimated from the length of the surgical tool and a measured distance between the light emitting device and the surgical tool handle.

In another exemplary embodiment, an estimated location of the tip of the surgical tool is visually presented on a graphical display. A 3D reconstruction and the target trajectory are visually presented on the graphical display with the estimated location of the tip of the surgical too.

DETAILED DISCLOSURE

Figure 1:
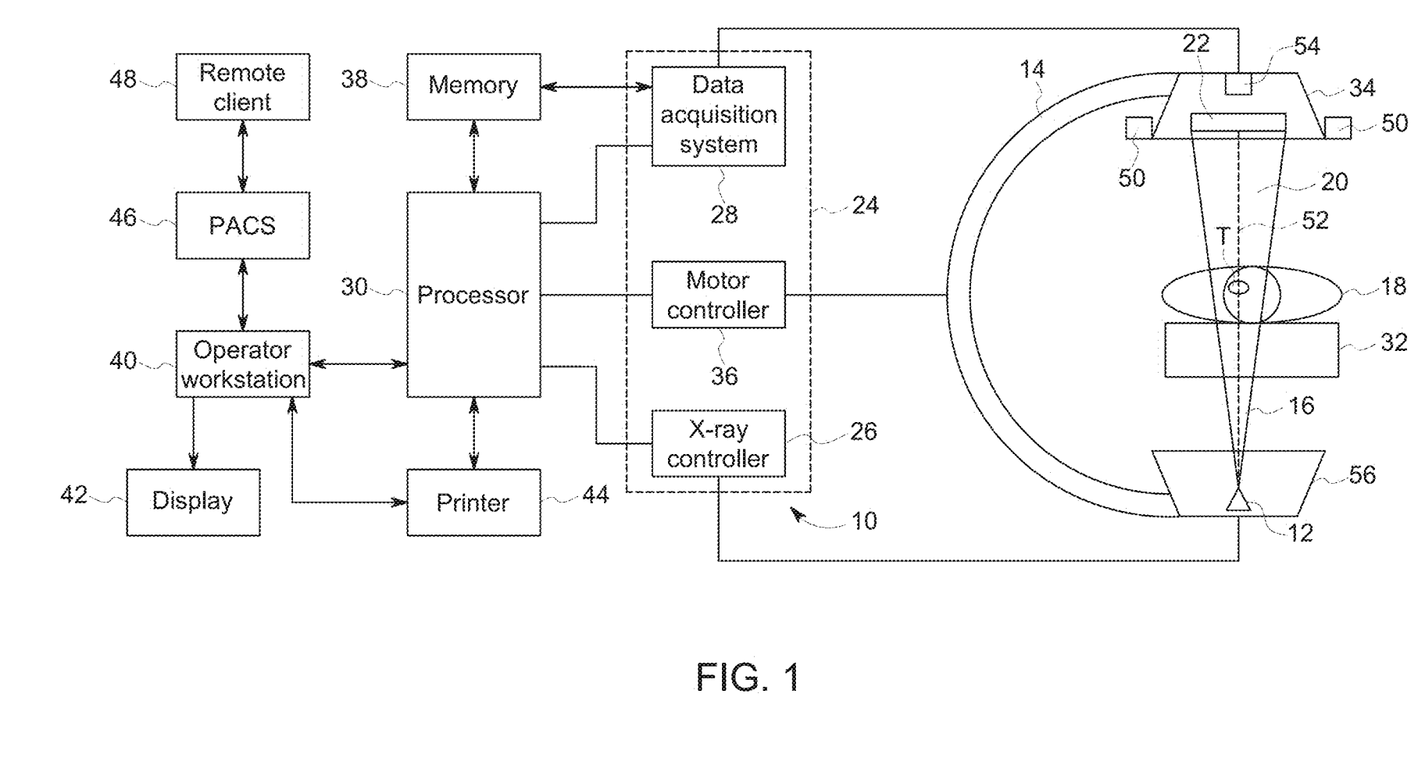
FIG. 1 s a system diagram of an exemplary embodiment of an imaging and navigation system.

FIG. 1 is a system diagram of an exemplary embodiment of an imaging and navigation system 10. In an exemplary embodiment, the system is configured for use as described as a surgical navigation system. The system 10 depicted in FIG. 1 is exemplarily embodied as a C-arm fluoroscopic imaging system, yet it will be understood by a person of ordinary skill in the art that other forms of imaging and/or navigation systems may be used within the scope of the present disclosure. The system 10 exemplarily acquires X-ray attenuation data at a variety of views around a patient and suitable for tomographic reconstruction. The system 10 includes an X-ray source 12 secured to a C-arm 14. The X-ray source 12 may exemplarily be an X-ray tube, a distributed X-ray source (such as a solid-state or thermionic X-ray source) or any other source of X-ray radiation suitable for the acquisition of medical or other images. The X-ray source 12 emits X-rays 16 in the direction of a patient 18. In the exemplary embodiment depicted, the X-rays 16 are emitted in a cone shape, i.e. a cone-beam. This cone-beam of X-rays pass through the imaged volume of the patient 18. An incident portion of the X-ray radiation beam 20 passes through or around the patient 18 and impacts a detector array 22. Detector elements of the detector array 22 produce electrical signals that represent the intensity of the incident X-rays 20. These signals are acquired and processed to reconstruct images of the features within the patient 18.

The X-ray source 12 is exemplarily controlled by a system controller 24 which furnishes both power and control signals for the operation of the imaging system. The system controller 24 exemplarily controls the X-ray source 12 via an X-ray controller 26 which may be a component of the system controller 24. In such an embodiment, the X-ray controller 26 may be configured to provide power and timing signals to the X-ray source 12.

The detector 22 is further exemplarily connected to the system controller 24. The system controller 24 controls the acquisition of the signals generated in the detector 22. In an exemplary embodiment, the system controller 24 acquires the signals generated by the detector using a data acquisition system 28. The data acquisition system 28 receives data collected by readout electronics of the detector 22. The data acquisition system 28 may receive sampled analogue signals from the detector 22 and convert the data to digital signals for subsequent processing by a processor 30 discussed in further detail herein. Alternatively, in other embodiments, the analogue to digital conversion may be performed by circuitry provided on the detector 22 itself. The system controller 24 may also execute various signal processing and filtration functions with regard to the acquired image signals, such as, but not limited to, initial adjustment of dynamic ranges and interleaving of digital image data.

The system controller 24 is further operationally connected to the gantry C-arm 14 as well as to a table 32 configured to support the patient 18. A motor controller 36 of the system controller 24 provides the instructions and commands to the mechanical components of the C-arm 14 and the table 32 to carry out linear and/or rotational movement thereof. The linear and/or rotational movement of the C-arm 14 enables the X-ray source 12 and the detector 22 to be rotated about the patient one or multiple turns around the patient 18, such as rotated primarily in an X, Y-plane or angulated with respect to the patient. In other embodiments of imaging devices, the source and detector may be rotated multiple times about the patient. The distance between the detector 22 and the X-ray source 12 can also be adjusted. The table 32 supporting the patient 18 can also be ordinately moved with respect to the movement of the C-arm and/or planned movement of the C-arm to position the patient within the imaging field of view of the imaging system 10. Thus, movement of the patient and/or components of the imaging system to adjust the imaging field of view may include one or both of movements of the C-arm 14 and the table 42.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about an area of interest or target T so that X-ray attenuation data may be obtained at a variety of views relative to the target T. In the present context, system controller 24 may also include signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to a processing component 30 for reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image reconstruction, as described below. One example of image reconstruction may include cone beam computed tomography (CBCT) wherein images acquired at multiple angles about the patient 18 by the source 12 and the detector 22 are projected against each other to form voxels of a 3D representation of the imaged region. A person of ordinary skill in the art will recognize other forms of image reconstruction, including but not limited to processing image data from the detector signal to produce clinically useful images.

The processing component 30 may be configured to receive commands and scanning parameters from an operator via an operator workstation 40, typically equipped with a keyboard, touchscreen and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

The system 10 additionally includes at least one light source. The at least one light source may exemplarily be at least one laser 50 although it will be recognized that other light sources, including those emitting coherent or incoherent light, may be used within the scope of the present disclosure. Additionally, as disclosed in further detail herein, embodiments may use one light source, two light sources, or more than two light sources, although the exemplarily embodiment provided in FIG. 1 depicts two lasers 50. The lasers 50 are mounted at the detector end of the C-arm 14 in an area about the detector 22. The lasers 50 can be secured relative to the detector 22 in any suitable manner such that the lasers 50 are located in an offset position relative to an axis 52 of the X-ray beam 16 between the X-ray source 12 and the detector 22. The lasers 50 can be mounted directly to the detector 22, such as within a housing for the detector 22, or to the exterior of the detector 22, or to another portion of the C-arm 14, for example using a suitable support arm or other similar apparatus which may be, but is not limited to, a collapsible or full-way support apparatus. In still further exemplary embodiments, the lasers 50 may be removable from engagement with the detector 22 or the C-arm 14 by mechanical, magnetic, or other suitable supporting devices.

The lasers 50 may include batteries (not depicted) to power the lasers 50 while in other exemplary embodiments, the lasers 50 may be powered by the same power sources (not depicted) as the detector 22 and/or C-arm 14. In an exemplary embodiment, the power, control, and sensing signals used for the positioning and operation of the lasers 50 can be provided by the system controller 24.

In exemplary embodiments, the lasers 50 may be operable to produce any of a variety of beams, including, but not limited to points, lines, or fan shaped beams. In one exemplary embodiment, at least one laser produces a line of laser light from a laser 50 to project a point on a surface, for example on the skin of the patient 18, such laser 50 being operable to align the laser beam with an insertion path or needle trajectory of a needle surgical procedure. In further exemplary embodiments as described herein, a laser 50 is operable to produce a fan shaped beam that projects a line on the body of the patient 18. The line and beam projected on the patient 18 may being alignable with the needle trajectory which may further assist in providing confirmation that a needle is aligned with the target trajectory by providing indication of such on the heel or handle end of the needle as described herein, but also by potentially providing a light projection on the side of the needle to assist in maintaining alignment with the target trajectory. In a still further exemplary embodiment, two lasers 50 are used to project two lines, forming a crosshair or a line and a point with which to align a needle along a trajectory.

Additionally, the system 10 includes a laser range meter 54. The distance meter 54 may exemplarily be a laser distance meter. The range meter 54 is positioned in relation to the one or more lasers 50 and operates to measure a distance between the range meter location and the surface upon which the laser is striking. In an exemplary embodiment, the range meter 54 may be located interior to or adjacent to the housing surrounding the detector 22, in a position similar to that of one or more of the lasers 50, and/or at a position relative to the C-arm 14.

As will be described in further detail herein, the X-ray detector 22 and the patient table 32 are positioned in a manner such as to make one or more laser beams from the one or more lasers 50 to coincide with a planned target trajectory for a needle surgical procedure. This alignment materializes as a point, line, and/or crosshair on the patient's skin at the needle insertion point prior to the needle tip positioning and once the needle has been inserted into the skin of the patient, the point, crosshair, or line is exemplarily materialized at a center of the needle handle during insertion of the needle along the planned trajectory. The range meter 54 operates in this system to measure the distance (DP) as explained in further detail herein from the laser source to the point P which is defined by the intersection of the laser line with an intersecting surface (e.g. patient skin or needle handle). This measurement of distance variation before and during the needle insertion procedure provides the ability to locate the point P in the coordinate system of the X-ray imaging system to achieve the additional functionalities as described in further detail herein.

The imaging system 10 as described above may exemplarily be used in a variety of functions and embodiments, examples of which are provided herein which will provide additional exemplary and non-limiting disclosure. Three functional embodiments which will be described in further detail herein include surgical tool navigation, skin surface location and mapping, and an augmented reality referential system. FIGS. 2-6 exemplarily depict embodiment of a surgical tool (e.g. needle) navigation.

Figure 2:
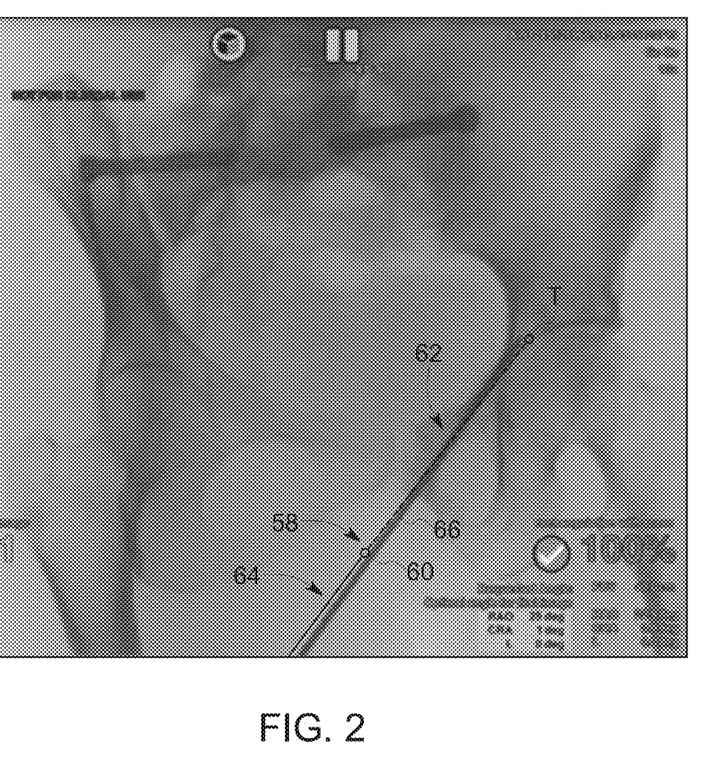
FIG. 2 depicts an exemplary embodiment of a screen shot of a 3D image of needle guidance in a surgical procedure.

FIG. 2 depicts an exemplary embodiment of a screen shot of a 3D image of needle navigation in a surgical procedure. The planned needle target trajectory 58 is represented in the 3D image of the patient, which may exemplarily be based upon previously acquired X-ray images of the patient. The planned needle target trajectory 58 is exemplarily represented as a bifurcated line. The line 58 is bifurcated at the insertion point 60 exemplarily denoting the skin of the patient. Thus, the trajectory 58 includes an internal portion 62 and an external portion 64. In current needle guidance systems fluoroscopy or other intermittent acquisition of X-ray images is used to acquire a needle image 66 which is presented with respect to the planned trajectory 58. However, in embodiments as described herein, no or fewer X-ray images need to be acquired to confirm needle location as the needle position relative to the planned trajectory 58 can be estimated with a high degree of accuracy.

Figure 3:
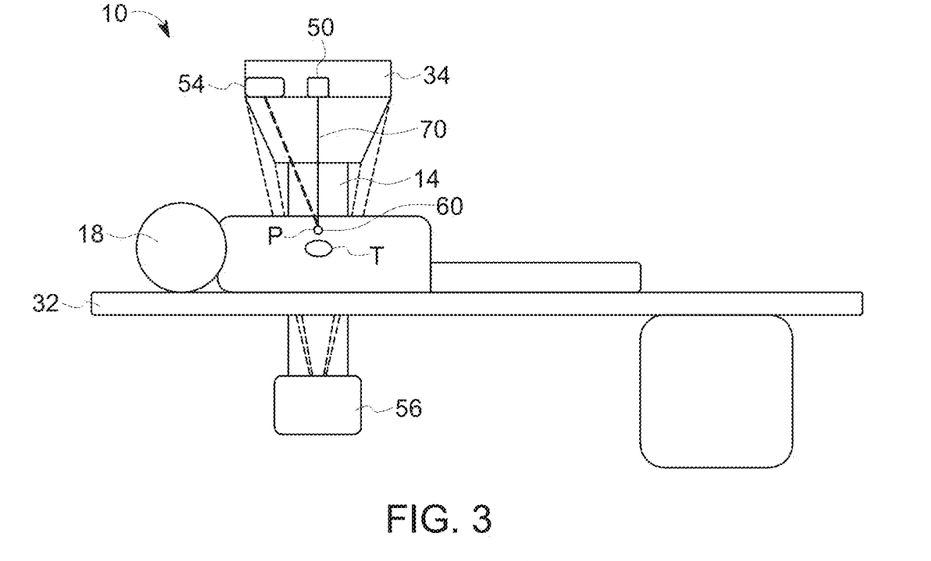
FIG. 3 is an exemplary side view of a patient in a needling procedure.
Figure 4:
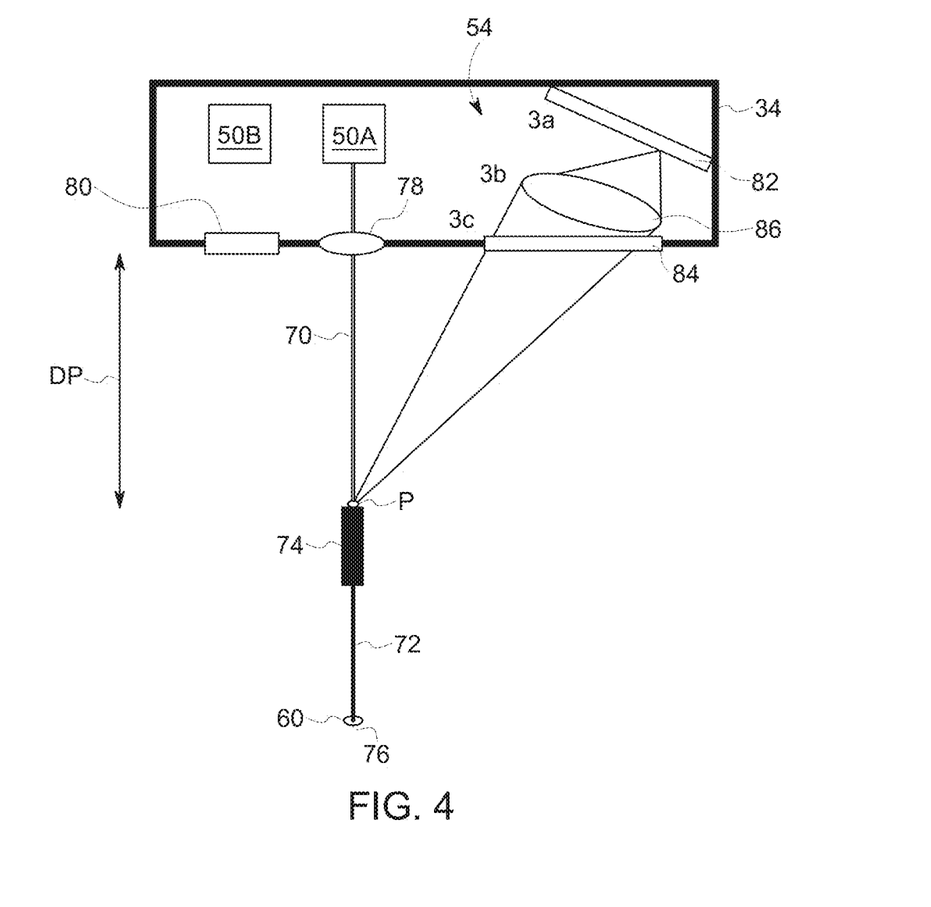
FIG. 4 is a detailed schematic view of an exemplary embodiment of a surgical navigation system.

FIG. 3 is an exemplary side view of a patient positioned relative to an imaging and navigation system 10 to undergo a needling surgical procedure. It will be recognized that like reference numerals are used herein to reference like structures as described above with respect to FIG. 1. In the side view provided by FIG. 3 the C-arm 14 includes the detector housing 34 and the X-ray source housing 56. The C-arm 14 positions these elements about the patient 18 and relative to a target T. A laser beam 70 is emitted from the laser 50 in the direction of the target T. The C-arm 14 rotates to position the laser beam 70 in alignment with the planned needle target trajectory. With alignment of the laser beam 70 with the planned needle target trajectory, the incidence of the laser beam 70 in the skin surface of the patient 18 provides a point P at the insertion point 60 of the planned needle target trajectory. A range meter 54 obtains an estimate of the distance DP from the laser source 50 to the point P which may be used, as described in further detail herein, for example to facilitate registration between the trajectory planning images (as depicted in FIG. 2) and the patient 18 and/or new images acquired by the imaging system 10. This may occur, for example, when the images acquire less than the entirety of a cross-section of the patient. FIG. 4 is a detailed partial schematic view of the surgical tool navigation system depicted in FIG. 3. As depicted in FIG. 4, the needle 72 is aligned with the laser beam 70 along the planned needle target trajectory such that the laser beam 70 impinges on the handle 74 of the needle 72 at point P. It will be understood that at least a portion of the needle 72 and the handle 74 now separate the point P from the insertion point 60. If a tip 76 of the needle 72 is located at the insertion point 60, the needle 72 has not been inserted into the patient yet. While if the tip 76 is internal to the patient, then the point P at the handle 74 of the needle 72 will move closer to the insertion point 60 on the skin of the patient.

Thus, during a needling procedure, the distance DP between the laser source and the point P will be less than the distance DP when no needle is present. As will be described in further detail herein, this change in distance DP can be used to provide an estimate of the progression of the needle tip 76 along the planned target trajectory and thus provides an estimation as to the location of the needle tip 76 within the patient and when the needle tip 76 has reached the target T.

FIG. 4 further includes a more detailed schematic view of an exemplary embodiment of components which may be located internal the detector housing 34. It will also be recognized that the components as depicted in FIG. 4 may also be located in a separate housing or within other locations relative to the gantry (not depicted) while remaining within the scope of the present disclosure.

The laser beam 70 is provided by laser source 50A which exemplarily projects a line beam of laser light. However, it will be recognized that in other embodiments as described herein, the laser source 50A may project a fan beam of laser light. The line beam of laser light projected from the laser source 50A is projected through optics 78 to focus the line beam. In an additional exemplarily embodiment, the imaging system may further include one or more additional laser sources 50B. The additional laser source 50B may exemplarily be a fan beam laser source which may project such fan beam (not depicted) through a diverging lens 80 which is configured to diverge the fan beam in a plane for example perpendicular to the figure which provides an alignment line in conjunction with the point P provided by the laser beam 70. If multiple additional laser sources 50B are provided, then the lines of the fan beam may provide a crosshair. In a still further exemplary embodiment, the intersection of crosshair provided two or more fan beams may form point P as used in embodiments as described herein. As further depicted and described herein with respect to FIGS. 11A and 11B, when two or more fan beam laser sources 50A, 50B are provided, the intersection of the fan beams can produce both a cross hair on the patient, as well as a line denoting a target trajectory as described in further detail herein.

The range meter 54 may exemplarily include a linear sensor 82. The linear sensor may exemplarily be a CMOS chip or a CCD camera or other sensors as may be recognized by a person of ordinary skill in the art. A transparent window 84 permits the laser light reflected off the handle 74 to enter the housing 34 while protecting the elements contained therein. A converging lens 86 collects the reflected light and directs it to the linear sensor 82 which based upon the location of the converged reflected light, is able to produce an indication of the distance of the point P from the source 50A. In this manner, the system is able to track the relative position of the point P and thus the tip of the needle 76 if the needle dimensions are known.

Figure 5:
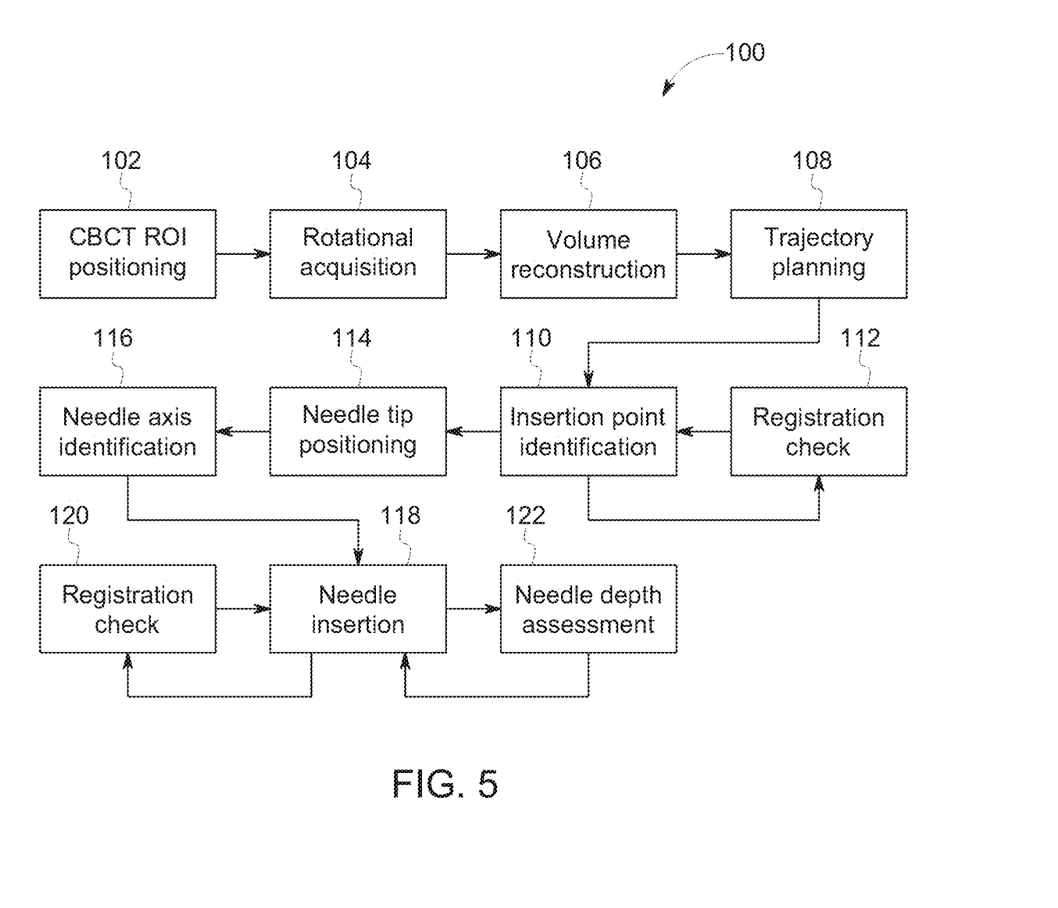
FIG. 5 is a flow chart that depicts an exemplary embodiment of a work flow method for needle guidance.

FIG. 5 is a flow chart that depicts an exemplary embodiment of a work flow method 100 for guidance of a surgical tool, for example a needle. It will be recognized that portions of the method 100 are facilitated or carried out with exemplary embodiments of the features and structures as disclosed herein.

The method 100 exemplarily includes at 102 positioning an ROI of a CBCT imaging procedure relative to the target T. By identifying the location of target T and positioning a CBCT/ROI relative to the target, a rotational acquisition at 104 of a series of CBCT projection images, for example as carried out by operation of the imaging system 10 including the C-arm 14, X-ray source 12, and X-ray detector 22, as all described above with respect to FIG. 1. From the acquired CBCT projection images, a 3D volume reconstruction may be performed at 106. In the 3D volumetric reconstruction, any of a variety of reconstruction techniques may be used which are suitable to create a 3D image from a series of 2D projection images. Once a 3D reconstruction of the region of interest (ROI) about the target T is created, trajectory planning at 108 may be used to calculate and identify a preferred needle target trajectory for use in carrying out the needle procedure.

With the target trajectory defined, the C-arm is operated to align at least on laser beam from at least one of the laser sources with the target trajectory. The position wherein the laser beam in alignment with the target trajectory impinges upon the skin of the patient identifies the insertion point of the needle into the patient at 110. At 112 this identification of the insertion point can be considered and evaluated against the planned needle target trajectory. In an embodiment, this can serve as a registration check to confirm registration between the planned needle target trajectory and the alignment of the patient with the imaging and guidance system. In an exemplary embodiment, one or more confirmation images may be acquired with the imaging system to facilitate in this registration check.

At 114, the clinician positions the needle tip at the insertion point. After the needle tip is positioned at the insertion point then the clinician moves the needle until one or more laser lines are projected on the handle of the needle in order to identify at 116 that the needle is in alignment with the axis of the needle target trajectory. In an embodiment, the needle is positioned until the center of the crosshair is visible at the top of the handle of the needle and the two fan beams projected along the shaft of the needle. With visual confirmation that the needle is in alignment with the needle trajectory, the clinician can begin insertion of the needle at 118. At 120, images may be acquired as registration checks to confirm estimated needle tip positions and to update any position of the needle tip and/or alignment with the patient. At 122, the identified position of the needle handle as measured in the manner as described in further detail herein and by way of use of the distance meter enables estimates of the needle tip position along the needle trajectory towards the target T.

Figure 6:
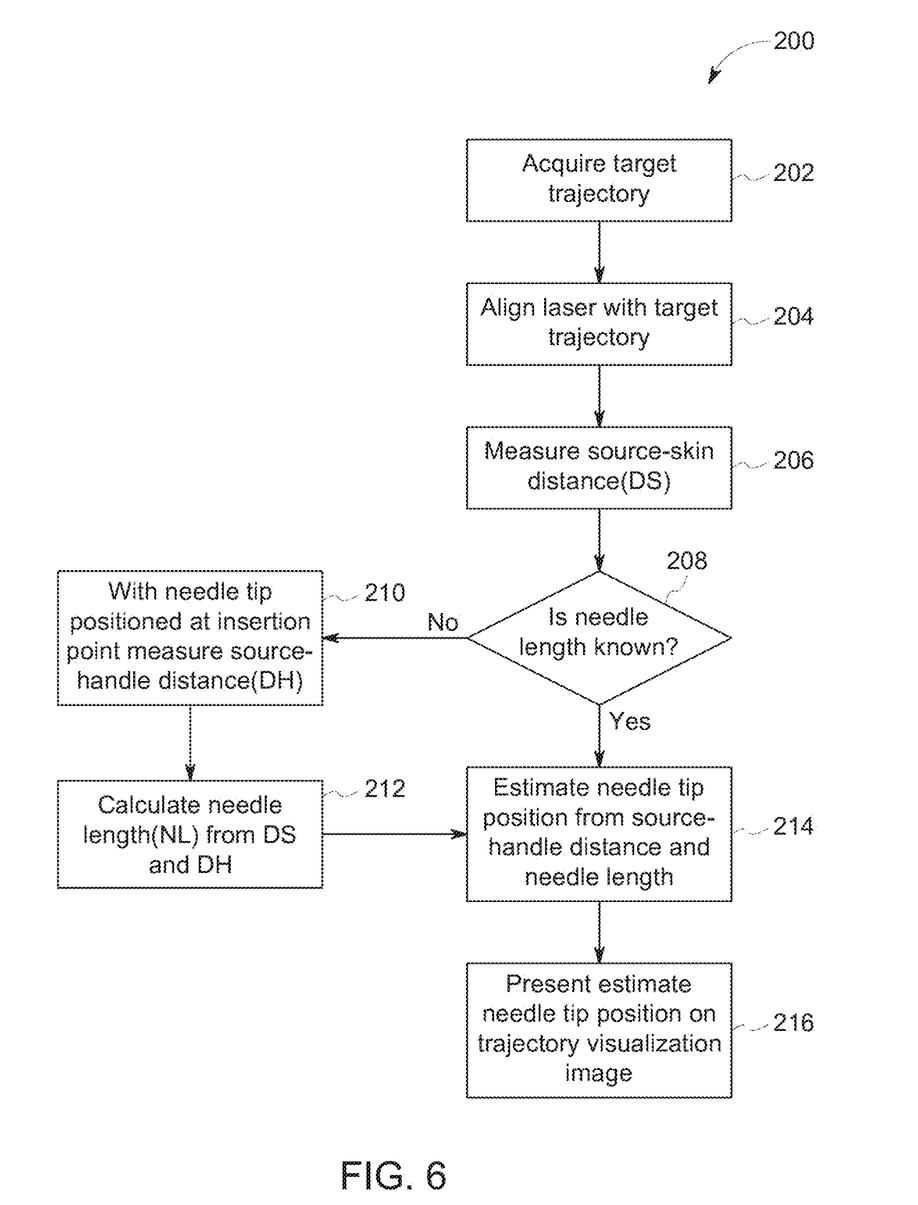
FIG. 6 is flow chart which depicts an exemplary embodiment of a method of surgical tool navigation.

FIG. 6 is an additional flow chart which depicts an exemplary embodiment of a method 200 of surgical tool navigation using the systems and methods as described herein.

At 202, the target trajectory for a planned needle surgical procedure is acquired. The target trajectory may exemplarily include a representation of the target trajectory in a 3D volumetric reconstruction of a region of interest of the patient about target T. The target trajectory may provide a preferred needle line or path from the skin of the patient to the target T and extend such path outward from the skin of the patient.

With the target trajectory acquired, then at 204, the C-arm 14 or other structures carrying the one or more laser sources can be moved in order to align at least one laser beam with the target trajectory. It will be recognized that the at least one laser beam aligned with the target trajectory may exemplarily be a crosshair formed of two generally orthogonal fan beams. With the at least one laser beam aligned with the target trajectory at 204, then the point at which the laser beam impinges upon the skin of the patient, exemplarily coincides with the insertion point from the target trajectory. A range meter of the imaging system can measure, at 206, a source-skin distance (DS). The range meter can identify the location of the light point created by impingement of the laser beam on the skin of the patient and triangulates a distance between that light point and the laser source projecting the beam. It will be recognized that the location of the light point can be identified and the distance between the light point and the laser source determined in other manners as well including, but not limited to: phase shift or time of flight techniques.

Next at 208, if the needle length is known, then the method 200 can proceed by acquiring the known needle length, exemplarily from a clinician input or by accessing such information from a database comprising needle length information.

If the needle length is not known, then a needle length may be measured by way of a comparison. At 210, with the needle tip positioned at the insertion point on the patient, and the needle in alignment with the needle trajectory, the range meter is used to measure a source-handle distance (DH). The source-handle distance (DH) is exemplarily measured from the light point on the handle created by impingement of the laser beam representing the target trajectory onto the handle of the aligned needle. The range meter measures the distance between that light point and the laser source. With the source-skin distance (DS) known and the source-handle distance (DH) known, the length of the needle (NL) may exemplarily be calculated by:

$$NL = DS - DH \quad (1)$$

In a still further exemplary embodiment, the imaging system may provide a calibration routine, suitable for measuring needle lengths by a similar method as described above with respect to 210 and 212. Exemplarily, a known reference point on the table 32 may be used in place of the insertion point as this may exemplarily eliminate a source of error exemplarily due to contact pressure and skin deformation resulting from contact between the needle and the skin of the patient.

At 214, before needle insertion and during needle insertion, estimates of the needle tip position are calculated in a similar manner as described above with respect to 210 and 212 as the needle tip position (TP) is exemplarily calculated as: TP=DH+NL. The combined SH+NL distance is taken along the needle trajectory from the laser source and at 216 is exemplarily represented on a trajectory visualization image, for example a three-dimensional reconstruction of the region of interest about the target T.

Figure 7:
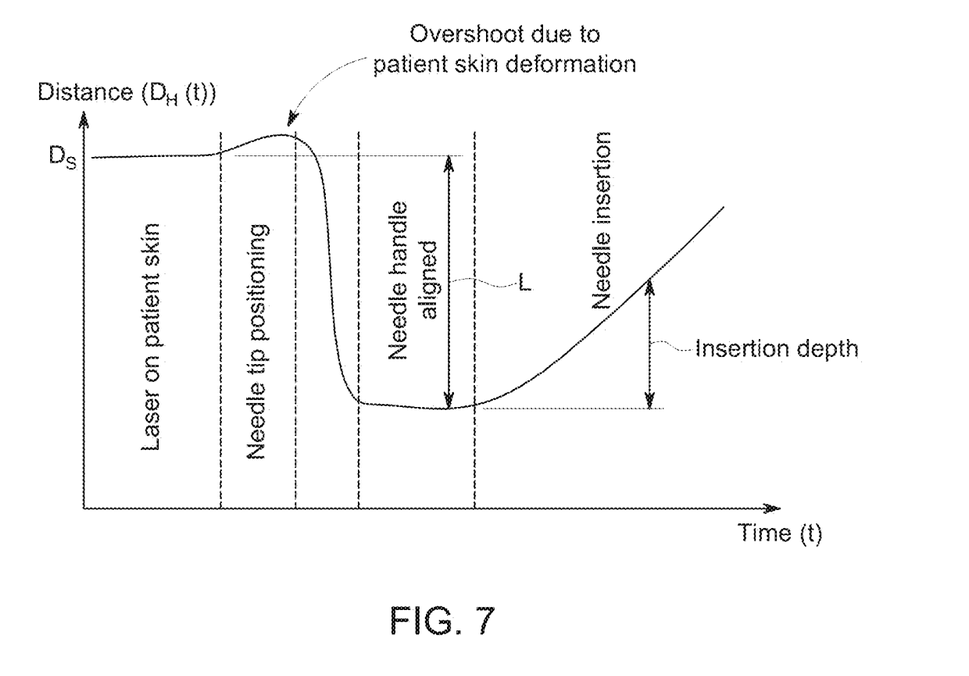
FIG. 7 is a graph that depicts an exemplary embodiment of relevant distances measured during a surgical navigation.

FIG. 7 is a graph that depicts an exemplary embodiment of relevant distances measured during a surgical tool navigation procedure. As depicted in FIG. 7, DS is the distance from the laser source to the insertion point represented on the patient skin. The distance from the laser to the handle of the needle (DH) is graphed on FIG. 7 over time DH(t). In the exemplary embodiment, time t=0 corresponds to the initial needle alignment with the needle trajectory prior to initial insertion. As explained above, the equation DS−DH(t) is used to calculate the needle length (NL) and the estimated needle tip position (TP) may be derived at any time from the DH(t) and needle length NL. As explained above, if the needle length (NL) is known, for example due to a manufacturers specification, then the estimated needle tip position (TP) can be derived from the measured DH(t) only in addition to the known NL value.

$$TP = DH(t) - NL \quad (2)$$

While knowledge of the needle length simplifies the initial alignment procedure by eliminating such calibration steps as needed to measure needle length, one draw back is to require specifying needle length to the system, for example by a clinician input or maintaining a database of needle types and dimensions for selection and acquisition. After the initial alignment, an assessment may be made as to whether the needle is kept in alignment or whether the physician obstructs the laser beam by monitoring the changes in measured DH(t). The changes in DH(t) should be consistent with clinician progression of the needle tip towards target T.

In exemplary embodiments, alarms can be set and initiated if it is detected that the needle handle has moved from the target needle trajectory.

In exemplary embodiments, as depicted and described herein, navigation of the needle along the needle trajectory to the target T may be guided solely through the use of the laser sources and distance meter and incases without reference to further X-ray or fluoroscopic images, limiting patient radiation dose required for needle guidance. In still further exemplary embodiments, if the needle is detected to drift from the target needle trajectory or if the needle tip is determined to be close or at the target T, the system may recommend to the clinician that X-ray, fluoroscopic, or other imaging be used to confirm needle positioning and location at the target T before completing the procedure.

Figure 8:
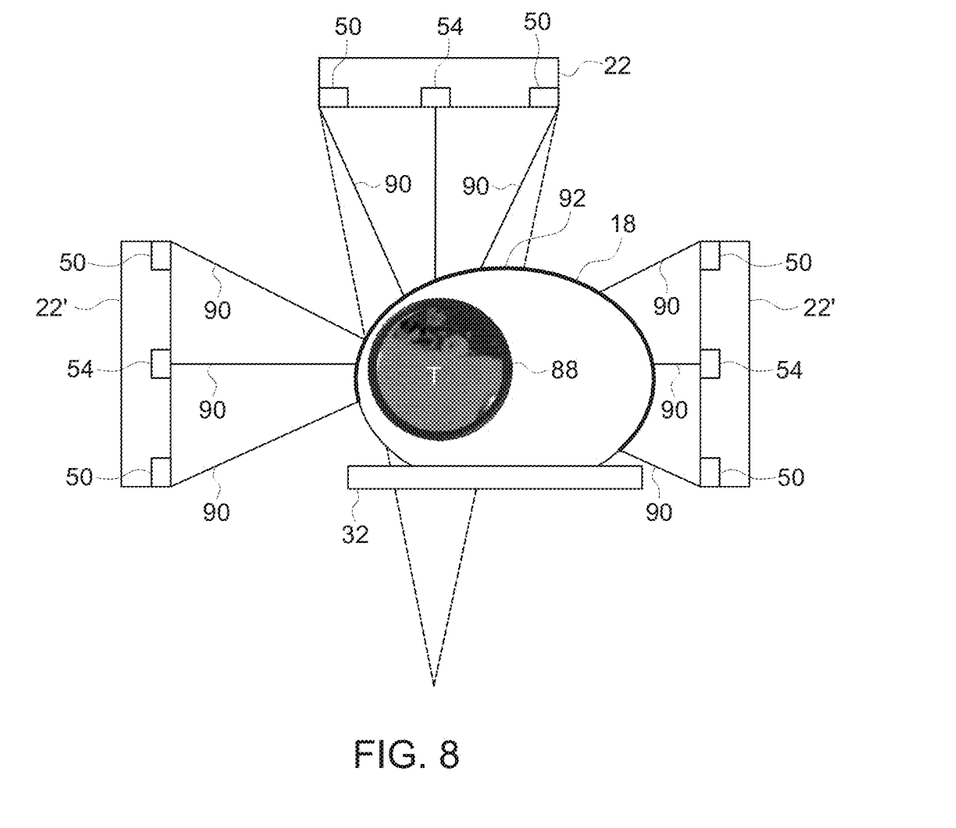
FIG. 8 depicts a schematic diagram of an exemplary embodiment of the imaging system.

FIG. 8 is a schematic diagram of an exemplary embodiment of the imaging system 10 used to image a target T within a patient 18. In an exemplary embodiment, a CBCT field of view (FOV) for 3D reconstruction is typically smaller than the cross sectional volume of the patient 18, especially across the chest of a patient 18. In an exemplary embodiment, the detector 22 which exemplarily rotates about the patient 18 between detector positions 22' may exemplarily be able to produce a CBCT FOV 88 which is sufficient to image target T, yet does not include the full extent of the cross section of the body of the patient 18. In an exemplary embodiment, one or more laser beams 90 project from the laser sources 50 and detected by the distance meter 54 are used in the manner as described herein in order to map the surface 92 of the skin of the patient 18 relative to the acquired CBCT images and such map position of the surface of the skin used to contextually locate the CBCT FOV 88 within a representation of the outer extent of the body of the patient 18. In an exemplary embodiment, the laser range meter can be used to locate the position of the patient skin during CBCT imaging. In one such exemplary embodiment, at any position of the detector 22, at least one point on the patient's skin surface can be located within the detector frame. As previously described, in embodiments, multiple lase sources may be provided relative to the detector 22 and thus embodiments using multiple laser sources may be able to map or monitor multiple points on the patient's skin during a single imaging procedure. In an exemplary embodiment using multiple laser sources, the laser sources may be arranged or oriented such that they do not overlap or interfere with one another over the entire range of useful measurement.

In the exemplary embodiment of CBCT acquisition, the skin surface can be mapped by monitoring the position of the impingement of the laser beams on the skin surface along the rotational trajectory. In an exemplary embodiment, the position of the table 32 (e.g. a table top) is known and an entire line of DS distances per laser source can be mapped during the imaging process. Assuming that the imagining system rotates along a longitudinal access of the patient/table, multiple laser sources e.g. laser sources positioned on each side (e.g. four sides) of the detector, can be used to map multiple circumferences on the patient's skin. If the laser sources are not arranged symmetrically, it is recognized that the laser source themselves will not provide redundant information as the detector rotates about the patient. As previously mentioned, in embodiments wherein CBCT acquisition provides limited 3D FOV due to the limited detected dimensions and space about the patient for imaging, it is difficult to reconstruct the skin surface of the patient from acquired images alone, particularly for the patient's thorax and abdomen. In exemplary embodiments, since the surface, particularly at the thorax and abdomen is relatively smooth, a combination of the distance measurements to the laser impingements on the skin combined with modeling as described herein (e.g. bilinear or bicubic interpolation) can provide reasonable accuracy to a patient circumference shape in a shape builder modeling as described herein.

An exemplary embodiment of a patient shape can also be obtained from the use of prior information in the patient electronic medical record (EMR). This prior information may exemplarily include diagnostic CT images and/or patient height and weight. The prior information of the patient can be combined with the sparse sampling provided by the measured laser impingement on the skin of the patient to reconstruct a more accurate skin surface and/or to quantify any potential error introduced by a simple interpolation as opposed to more complex modeling techniques as disclosed herein. In still further embodiments, it can also be used for extrapolating to areas where no distance measurements are available.

In an exemplary embodiment, after a skin surface has been obtained in the manner as described above, the distance measurement of the multiple lasers can be used to detect patient movement and deformation. These corrections can be especially valuable in embodiments prior to and during needle insertion as patient motion may introduce inaccuracy between the registration of the planned needle trajectory and the aligned laser position. In still further exemplary embodiment, wherein multiple laser sources are provided in the imaging system, the distance measurements from lasers that are not in use to guide the needle in the manners as previously described can be used for such motion detection and correction. For example, a measured laser source skin distance can be compared to an expected distance to the estimated skin surface location for each of the other particular laser sources associated with the detector. In an exemplary embodiment, a threshold may be provided that is useful to provide a meaningful limit upon which an alarm may be generated. In still further exemplary embodiments, at any moment during the needle guidance operation, the position of the patient skin as determined from reference to any of the laser beams impinging on the patient's skin from any of the other lasers sources can be compared to a position of the same laser beam during the acquisition of the 3D image used for planning the needle intervention. This comparison may be used to detect or estimate the moment or position within the patient breathing cycle where the target in the patient will match the location of the target T within the planning volume.

In an exemplary embodiment, as there are multiple patient support positions which allow alignment of one or more of the laser beams with the planned needle trajectory, in some embodiments an optimal patient support position may be determined to select between the available laser beams for needle guidance while selecting other laser beams for detection of patient motion. In an exemplary embodiment, a laser may be selected to be projected to a position on a patient where a small variation of the patient position will result in a large change in the laser distance measurement, making the laser distance measurement more susceptible to patent movement.

Figure 9:
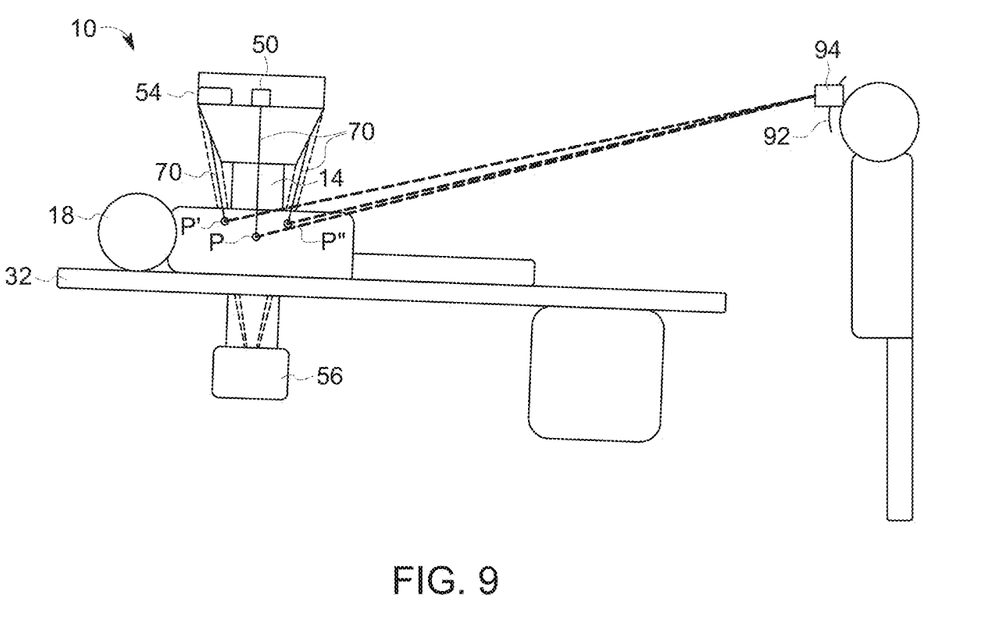
FIG. 9 depicts a still further exemplary embodiment of use of the laser alignment and guidance system in an augmented reality system.

FIG. 9 depicts a still further exemplary embodiment of use of the laser alignment and surgical tool 10 guidance system as described in further detail herein. In an exemplary embodiment, it will be recognized that the imaging and guidance system 10 depicted in FIG. 9 is similar in construction to that as depicted with respect to FIG. 3. As depicted in FIG. 9, the imaging and guidance system 10 may be used in an exemplary embodiment to provide fiducials for an augmented reality (AR) based guidance system. In an exemplary embodiment, in a needling procedure it exemplarily may be advantageous to keep the clinician's focus and attention directed towards the operating field, rather than turning the clinician's head/sight/attention to a display screen or monitor which is used to present the estimated needle tip position on a trajectory visualization image. In an exemplary embodiment using augmented reality wherein digital content is super imposed upon the visual perception of the real world by the clinician, using AR enabled glasses and/or other projection devices. Exemplarily, the clinician wears AR glasses 92 which project the digital content onto the retina of the user in combination of the received ambient light. One or more video and/or image capture devices 94 associated with the glasses 92 is used by a processor (not depicted) of the AR glasses 92 to gather information about the surroundings of the clinician. The augmented reality may exemplarily be used to enable the clinician to visualize the inner anatomy, exemplarily as provided form a 3D medical image (for example based upon CBCT) on the body of the patient 18, thus directly seeing the relative anatomy and exemplarily the needle target trajectory in relation to the imaged patient anatomy while being able to keep the needle in alignment and guide the needle in the manner as described above.

In an exemplary embodiment, the one or more of the laser sources, particularly those laser sources not in use to provide the needle trajectory are used to provide fiducials for registration of the 3D medical image data presented by the AR system to the body of the patient 18. In an exemplary embodiment wherein four laser sources are provided, one laser source may be used for representing the needle trajectory, while the other three laser sources are used to create three registration points which have a corresponding known position within a frame of the 3D medical image and map to the AR system frame, for example provided by the AR glasses 92. Scaling and registration between the medical image and the fiducials on the patient body 18 provided by the laser beams can be made to merge the 3D medical image onto the real world view of the patient 18. As noted above, in systems providing multiple laser sources, an optimization or selecting among the laser sources to determine which laser source or sources provide the needle trajectory and of which laser sources are used as the AR fiducials may be made. In an exemplary embodiment, the laser beams used as fiducials may be activated or operated individually so as to be recognized by the AR system and help with the registration processes. Exemplarily, this may be done using time coding between the laser beams or may be done using different laser wave lengths (e.g. frequency or color coding). As described above, one or more of the laser beams may also be used to provide the needle trajectory guidance, for example to provide an identification of the insertion point, monitor a patient location or patient movement, or to monitor a position of the needle handle to provide additional guidance an estimate of the needle tip position along the needle trajectory. In a still further exemplary embodiment, with knowledge of the estimated needle tip, a visualization of the needle within the patient 18 may further be provided in the AR system whereby the clinician is able to "observe the needle" for example by seeing a visualization of the estimated needle tip position relative to the 3D anatomy as presented in the AR visualization.

Figure 10:
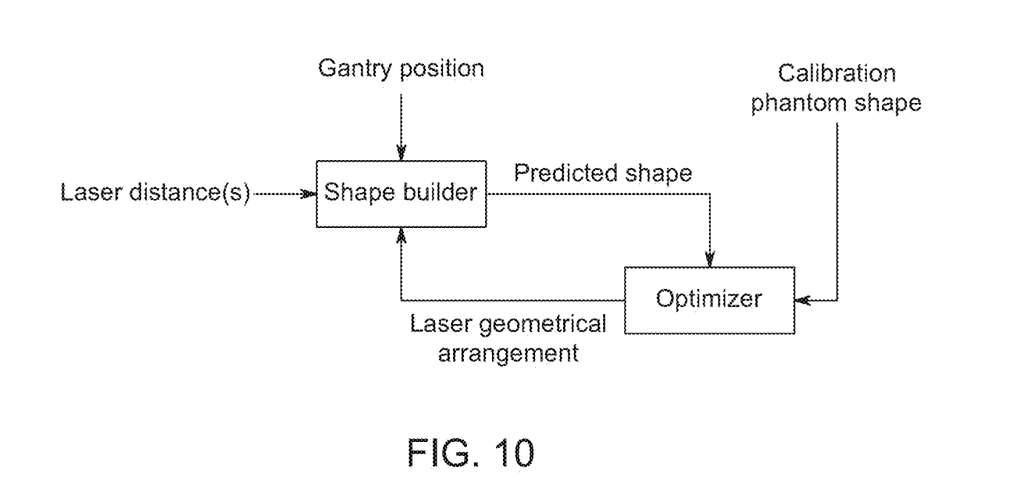
FIG. 10 is a schematic diagram of a exemplary embodiment of calibration of the lasers.

FIG. 10 is a schematic diagram of a exemplary embodiment of calibration of the lasers as may be used in exemplary embodiment of the systems and methods as described herein.

One challenge in exemplary embodiments as described herein includes accurately positioning the laser in space using a gantry intended to support an X-ray imaging system. Numerous factors may contribute to changes in the laser source position, including manufacturing tolerances and product aging may increase uncertainty surrounding exact laser source position. Therefore, calibration techniques and/or systems can be advantageous in order to provide adjustment of laser position as a function of the gantry and/or patient support positions. In such a calibration procedure, the laser position may be characterized in space for several gantry and patient support positions using a calibration phantom configured to receive lasers. Using prior art knowledge of the exemplary calibration phantom geometry, the calibration process can be used to determine a set of parameters to accurately derive the laser position as a transfer function of the gantry and patient support positions. In the exemplary embodiment, the calibration phantom as described above can also contain radio-opaque markers which may be detectable in X-ray projection images, for example in the X-ray projection images acquirable by the detector 22 of the imaging system 10. The X-ray projection images of the radio-opaque markers of the laser phantom can therefore provide a reference position of the phantom with respect to the X-ray beam of the imaging system 10. This may provide an augmented calibration between both the X-ray imaging system and the laser beam systems of the imaging system 10. By combining the calibration of the two systems in a single calibration procedure, the position of the laser beams with respect to the X-ray beam can become known which can be used to improve the accuracy of the needle guidance, skin mapping, and/or AR visualization of the patient's anatomy.

In an exemplary embodiment, laser distance meter technology may be based upon the use of triangulation. Laser distance measurements can be very accurate (possibly including sub-millimeter) in the distance range exemplarily considered (e.g. 100-500 mm). It will be recognized that in other embodiments, the range meter may be provided for example by using time of flight and/or phase shift, or other technologies as may be recognized by a person of ordinary skill in the art.

In further exemplarily embodiments, the laser source and the sensor optics may be packaged within a housing which exemplarily only contains the lenses sensor optics, and laser sources, while the electronics may be located remote to the optics. The laser sources and sensors may be arranged in a pattern that insures that each of the laser sources do not project a beam which interferes with any of the optics of any of the other laser systems within the useful operational range of the imaging system. In exemplary embodiments, at least one of the laser sources may produce a fan beam type laser beam. By incorporation of at least two fan beam projecting laser sources, the imaging system can produce a cross-hair light exemplarily for anatomy centering and/or for bullseye centering for laser guidance purposes. A fan beam laser should exemplarily be located exactly at a center of a detector side while in exemplary embodiments line beam generating lasers may be shifted to other positions about the detector without creating alignment issues. In exemplary embodiments, the fan beam laser source may be turned off when not in use so as to not create interference with distance sensors associated with one or more of the line beams. These exemplary embodiments may use this time coding to facilitate efficient operation of the system by limiting interference and promoting efficient use of laser sources.

In one exemplary embodiment, a line beam laser generator, two fan beam generators and a distance meter may be positioned to at least a minimum of two continuous sides of the detector to be able to selectively produce an alignment crosshair as well as to produce laser light line beams to carry out exemplary embodiments of the system and method as described herein. In an exemplary embodiment each of the laser sources may be individually controllable such as to selectively operate one or more of the lasers in combination.

Figure 11A:
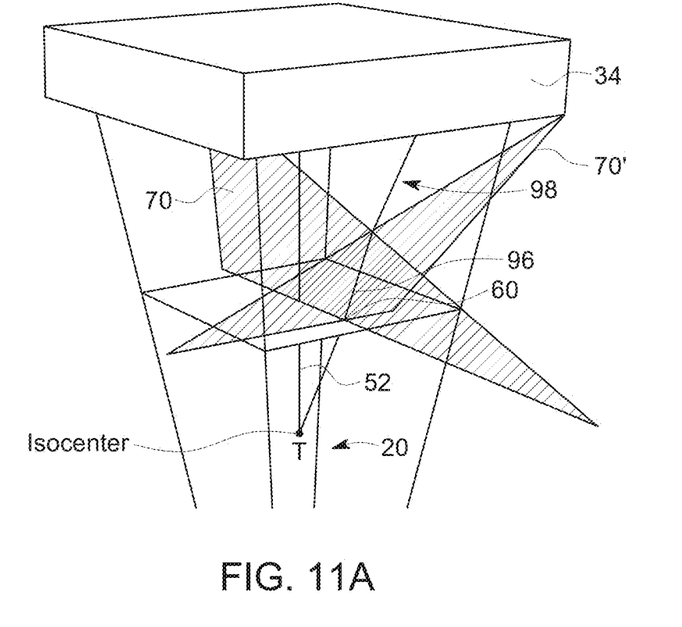
FIGS. 11A and 11B depict exemplary arrangements of light emitting devices in surgical navigation systems.
Figure 11B:
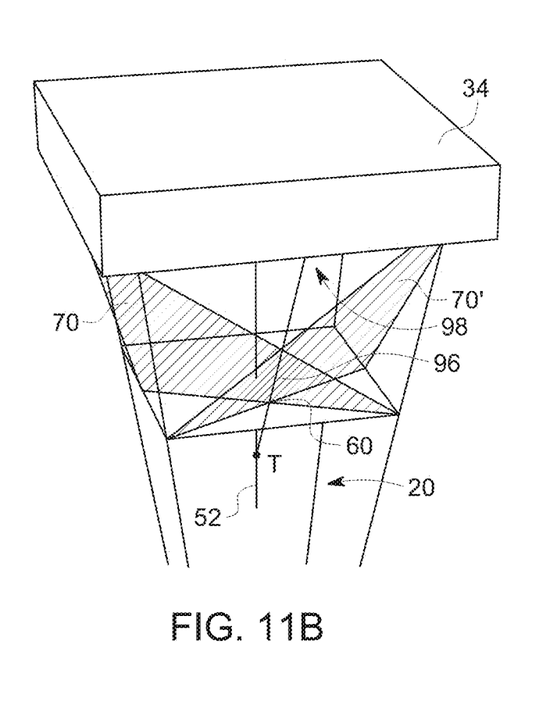

In still further exemplary embodiments, two fan beam laser sources may be used to create crosshair projections at the location of the needle. Each fan beam laser source projects light in a plane. Two laser sources are exemplarily positioned around the detector in a manner such that the two plains intersect at the trajectory line. Laser source locations are selected so that the two plains are projected in an generally perpendicular manner. This arrangement enables two lines to be projected on the sides of the needle in addition to the bullseye point on the needle handle. This may exemplarily further help the clinician to maintain needle alignment during insertion.

FIGS. 11A and 11B depict two exemplary embodiments of arrangements in which such a target trajectory line 96 may be provided with the combination of two fan beam planes 70, 70'. FIGS. 11A and 11B depict that fan beam lasers (70, 70') (or other laser sources) may be exemplarily located at opposite side of the detector housing (11B) or may be located at one corner and a middle of another side (11A). A person of ordinary skill in the art will recognize still further arrangements of positions for laser sources. FIGS. 11A and 11B further depicts that the target trajectory as represented by intersection 96 or laser beam 98 exemplarily extends in the absence of impingement on the patient's skin through a theoretical insertion point 60 to intersect the center 52 of the X-ray beam 20 at the target T.

In still further embodiments, a further lines beam 98 may also be used for centering. In such embodiments it may be advantageous to use two different colors or fast time switching (which may be exemplarily invisible to the clinician) scheme to allow for differentiation between the line beam laser 98 used for telemetry and the two lasers 70, 70' used for creating the crosshair. In a non-limiting exemplary embodiment, a red color may be used for the line laser 98 and a green color used for the fan beams 70, 70' which create the crosshair. This type of color scheme can further facilitate robust distance measurement in the presence of multiple light sources. In a still further exemplary embodiment, the telemetry system may be configured to reject any light out of a plane. Therefore, for example in a triangulation distance measurement system, one possible arrangement may be to orient the sensing system to point to a plane oriented at about 45° of the two crosshair plains, this being achieved using a narrow linear sensor and specific optics, and possibly using the addition of a collimation slit to the lens. Thus, the triangulation can be made without interference from the crosshair fan beams.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for surgical tool navigation, the system comprising:
    a movable gantry;
    a light emitting device connected to the moveable gantry and operable to project a point onto a surface, wherein the surface is a skin surface of the patient;
    a range meter connected to the gantry, wherein the range meter measures a distance between the light emitting device and the point projected on the surface;
    a system controller operatively connected to the movable gantry, wherein the system controller is configured to operate the moveable gantry to align a beam of light emitted from the light emitting device with a target trajectory for a surgical tool;
    wherein the system controller is configured to receive a measurement of a distance between the handle of the surgical tool and the light emitting device by the range meter when a tip of the surgical tool is placed at the point of impingement of the beam of light on the skin surface of the patient, and
    the system controller is configured to calculate the length of the surgical tool from the measured distance between the light emitting, device and the point of impingement of the beam of light on the handle of the surgical tool and the measured distance between the light emitting device and the point of impingement of the beam of light on the skin surface of the patient.

2. The system of claim 1, wherein the light emitting device is a laser source.

3. The system of claim 1, wherein the system controller calculates the target trajectory.

4. The system of claim 3, further comprising:
    an X-ray source configured to emit X-rays; and
    an X-ray detector configured to receive emitted X-rays to produce a plurality of projection images;
    wherein the system controller obtains the plurality of projection images, reconstructs a 3D image from the plurality of projection images, and calculates the target trajectory from the 3D image.

5. The system of claim 1 wherein the light emitting device is a first laser source, and further comprising a second laser source.

6. The system of claim 5, wherein the first laser source is a fan beam laser source and the second laser source is a fan beam laser source.

7. The system of claim 1, further comprising:
an X-ray source movably secured to the movable gantry and configured to emit X-rays; and
an X-ray detector movably secured to the movable gantry and configured to receive emitted X-rays; and
a system controller operatively connected to the movable gantry, the X-ray source, the X-ray detector, and the range meter, wherein the surface is a skin surface of the patient, the system controller operates to receive from the range meter, measured distances between the light emitting device and the skin surface of a patient as the gantry rotates on a rotational trajectory about the patient to acquire medical images of the patient, and the system controller maps the skin surface of the patient from the measured distances along the rotational trajectory.

8. A method of surgical tool navigation, the method comprising:
providing a movable gantry comprising a light emitting device and a range meter;
operating the light emitting device to project a beam of light at a surface, wherein the surface is a skin surface of the patient;
measuring a distance between a point of impingement of the beam of light on the surface and the light emitting device with the range meter;
aligning the beam of light with a target trajectory for a surgical tool by rotating the movable gantry;
measuring a distance with the range meter between the light emitting device and a point of impingement of the beam of light on a handle of the surgical tool when a tip of the surgical tool is placed at the point of impingement of the beam of light on the skin surface of the patient and
calculating the length of the surgical tool from the measured distance between the light emitting device and the point of impingement of the beam of light on the handle of the surgical tool and the measured distance between the light emitting device and the point of impingement of the beam of light on the skin surface of the patient.

9. The method of claim 8, wherein the surface is a surgical handle of the surgical tool and further comprising:
measuring a distance between the light emitting device and the point of impingement of the beam of light on the surgical tool handle with the range meter; and
estimating a location of a tip of the surgical tool along the target trajectory based upon the measured distance.

10. The method of claim 9 further comprising:
receiving a length of the surgical tool; and
estimating the location of the tip of the surgical tool from the length of the surgical tool and the measured distance between the light emitting device and the point of impingement of the beam of light on the surgical tool handle.

11. The method of claim 10 further comprising:
visually presenting the estimated location of the tip of the surgical tool on a graphical display; and
visually presenting a 3D reconstruction and the target trajectory on the graphical display with the estimated location of the tip of the surgical tool.

12. The method of claim 8, wherein the light emitting device is a line beam laser source and further providing a fan beam laser source on the movable gantry.

13. The method of claim 12, further comprising:
aligning a line beam from the line beam laser source with a target trajectory for a surgical tool; and
aligning a fan beam from the fan beam laser source along the target trajectory.

14. The method of claim 8 further comprising:
providing an X-ray source and an X-ray detector connected to the movable gantry, wherein the X-ray detector is connected to the light emitting device; and
operating the X-ray source and the X-ray detector to acquire a plurality of medical images as the movable gantry rotates the X-ray source and the X-ray detector on a rotational trajectory.

15. The method of claim 14 wherein the surface is a skin surface of a patient and further comprising:
measuring distances between the light emitting device and each of a plurality of points of impingement of the beam of light on the skin surface of the patient as the movable gantry rotates the X-ray source and the X-ray detector along the rotational trajectory; and
modeling a cross-sectional circumference of the patient from the measured distances.

* * * * *